(12) United States Patent
Yang et al.

(10) Patent No.: US 9,738,660 B2
(45) Date of Patent: Aug. 22, 2017

(54) SELECTIVE INHIBITORS FOR PROTEIN KINASES AND PHARMACEUTICAL COMPOSITION AND USE THEREOF

(71) Applicant: National Chiao Tung University, Hsinchu (TW)

(72) Inventors: Jinn-Moon Yang, Hsinchu (TW); Kai-Cheng Hsu, Hsinchu (TW); Tzu-Ying Sung, Hsinchu (TW); Shen Rong Lin, Hsinchu (TW); Yun-Ming Wang, Hsinchu (TW); Kuang-Mei Hsu, Hsinchu (TW); Hsin-Ping Lin, Hsinchu (TW); Wan-Chun Liu, Hsinchu (TW)

(73) Assignee: National Chiao Tung University, Taiwan (CN)

( * ) Notice: Subject to any disclaimer, the term of this patent is extended or adjusted under 35 U.S.C. 154(b) by 48 days.

(21) Appl. No.: 14/599,349

(22) Filed: Jan. 16, 2015

(65) Prior Publication Data
US 2016/0096848 A1  Apr. 7, 2016

(30) Foreign Application Priority Data

Oct. 3, 2014 (TW) .............................. 103134527 A

(51) Int. Cl.
*A61K 31/553* (2006.01)
*C07D 498/22* (2006.01)

(52) U.S. Cl.
CPC .................. *C07D 498/22* (2013.01)

(58) Field of Classification Search
CPC ........................... A61K 31/553; C07D 498/22
USPC ..................... 514/211.08; 540/545
See application file for complete search history.

(56) References Cited

U.S. PATENT DOCUMENTS 5,093,330 A * 3/1992 Caravatti ............. C07D 498/22
514/211.08
5,344,926 A * 9/1994 Murakata ............. C07D 498/22
540/545
5,674,867 A * 10/1997 Tamaoki ............. C07D 498/22
514/211.08

FOREIGN PATENT DOCUMENTS

WO   WO 93/07153   *   4/1993

* cited by examiner

*Primary Examiner* — Brenda Coleman
(74) *Attorney, Agent, or Firm* — Bryan D. Zerhusen; Locke Lord LLP

(57) ABSTRACT

The present invention provides a compound of formula (I) or the salt thereof:

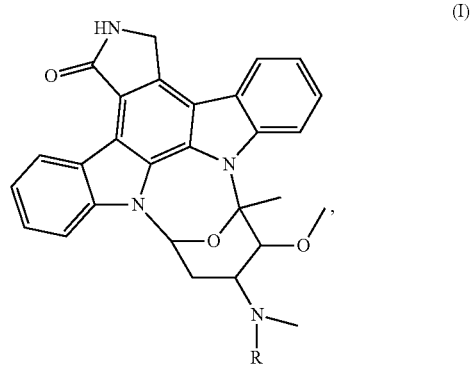

Figure 1:
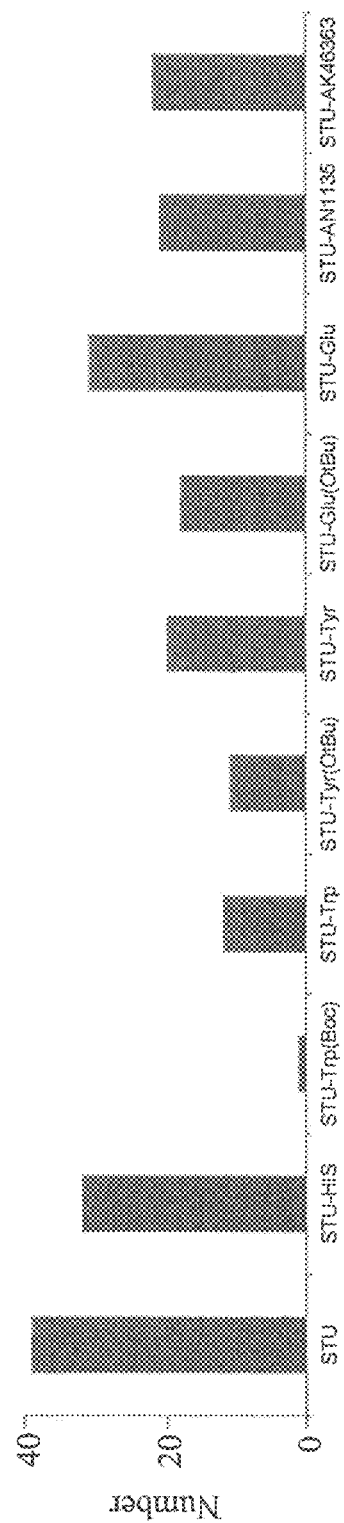

wherein R is at least one selected from the group consisting of unsubstituted $C_{1-4}$ alkyl, $C_{1-4}$ alkyl substituted by $C_{6-18}$ aryl or —$OR^1$, and —C(=O)Z. The compound is a type-S protein kinase inhibitor, which binds to an ATP-binding site and a substrate-recognition site of a protein kinase simultaneously. The present invention further provides a pharmaceutical composition, which includes a compound of formula (I) or a salt and a pharmaceutically acceptable carrier thereof. The present invention further provides a use of a compound of formula (I) or a salt thereof, which is for the manufacture of a protein kinase inhibitor as a drug.

5 Claims, 2 Drawing Sheets

SELECTIVE INHIBITORS FOR PROTEIN KINASES AND PHARMACEUTICAL COMPOSITION AND USE THEREOF

CROSS-REFERENCE TO RELATED APPLICATIONS

This application claims the benefit of Taiwan Patent Application No. 103134527, filed Oct. 3, 2014, the entire contents of the aforementioned application is hereby incorporated herein by reference.

BACKGROUND OF THE INVENTION

1. Field of the Invention

The present invention relates to inhibitors for protein kinases, and more particularly, to a type-S protein kinase inhibitor having a selective inhibitory effect on a protein kinase.

2. Description of Related Art

A protein kinase plays a critical role in an organism. Because protein kinases are often over-expressed in tumor cells, the inhibitions of the protein kinases can be used to control tumor growths. Currently, several protein kinase inhibitors have entered the stage of clinical trials. These inhibitors often inhibit many other protein kinases at the same time, leading to the occurrences of many side-effects, such as cardiotoxicity, anemia, thrombocytopenia, and the like. For example, the use of Sunitinib, a drug for treating renal cell carcinoma, inhibited 259 protein kinases (~68%) out of the 384 tested protein kinases. Therefore, the development of a highly specific protein kinase inhibitor is beneficial to the reduction of side-effects and treatment of cancers.

Currently, protein kinase inhibitors may be preliminarily classified into three major categories (including types I, II and III). The majority of the protein kinase inhibitors are type I inhibitors. A type I inhibitor mainly targets the DFG-in active conformation, and often directly competes for an ATP-binding site. Thus, the type I inhibitors lack selectivities. A type II inhibitor binds at an ATP-binding site, and an adjacent cleft created by the induction of DFG-out conformation. A type II inhibitor has an additional reaction with αC-helix and a DFG motif, such that it is relatively more selective. A type III inhibitor is a non-ATP competitive inhibitor, such that it interacts with the allosteric site of the DFG motif, adjacent to αC-helix of the active conformation. Several studies have shown the occurrences of drug-resistant mutations in the types I, II and III inhibitors. Hence, the development of a novel type-S protein kinase inhibitor may also provide a new starting point in the treatment of wild-type and drug-resistant cancers.

SUMMARY OF THE INVENTION

The present invention provides a compound of formula (I) or the salt thereof:

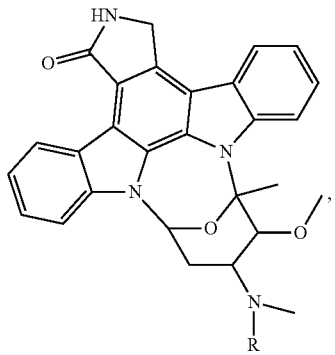

wherein R is at least one selected from the group consisting of unsubstituted $C_{1-4}$ alkyl, $C_{1-4}$ alkyl substituted by $C_{6-18}$ aryl or —$OR^1$, and —C(=O)Z;

$R^1$ is at least one selected from the group consisting of hydrogen, $C_{1-4}$ alkyl and

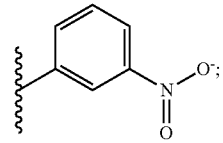

wherein Z is —$C(NH_2)CR^2$; and $R^2$ is at least one selected from the group consisting of unsubstituted phenyl, phenyl substituted by hydroxyl or $C_{1-4}$ alkoxyl, unsubstituted $C_{5-10}$ cycloheteroaryl, $C_{5-10}$ cycloheteroaryl substituted by $C_{1-4}$ alkoxycarbonyl, carboxyl, and an ester group.

The present invention further provides a pharmaceutical composition, which includes a compound of formula (I) of the present invention or a salt or a pharmaceutically acceptable carrier thereof.

The present invention further provides a method for inhibiting a protein kinase in an individual, which includes a step of administering an effective amount of a drug containing a compound according to the present invention or a salt thereof to the individual.

An objective of the present invention is to provide a use of a compound according to the present invention or a salt thereof, which is to manufacture a protein kinase inhibitor as a drug.

The present invention used staurosporine (hereinafter abbreviated as STU) as a core framework, which has an attached functional group mimicking the physicochemical properties of various protein kinase substrates and with a specifically designed molecular length. As a result, an obtained type-S protein kinase inhibitor occupies an ATP-binding site and a substrate-recognition site of a protein kinase at the same time, such that the effect of a high selectivity for inhibiting a protein kinase was achieved. The compounds of formula (I) of the present invention showed highly selective inhibitory effects on specific protein kinases and possibly further effectiveness in the inhibition of the growth of tumor cell lines.

BRIEF DESCRIPTIONS OF THE DRAWINGS

Figure 2:
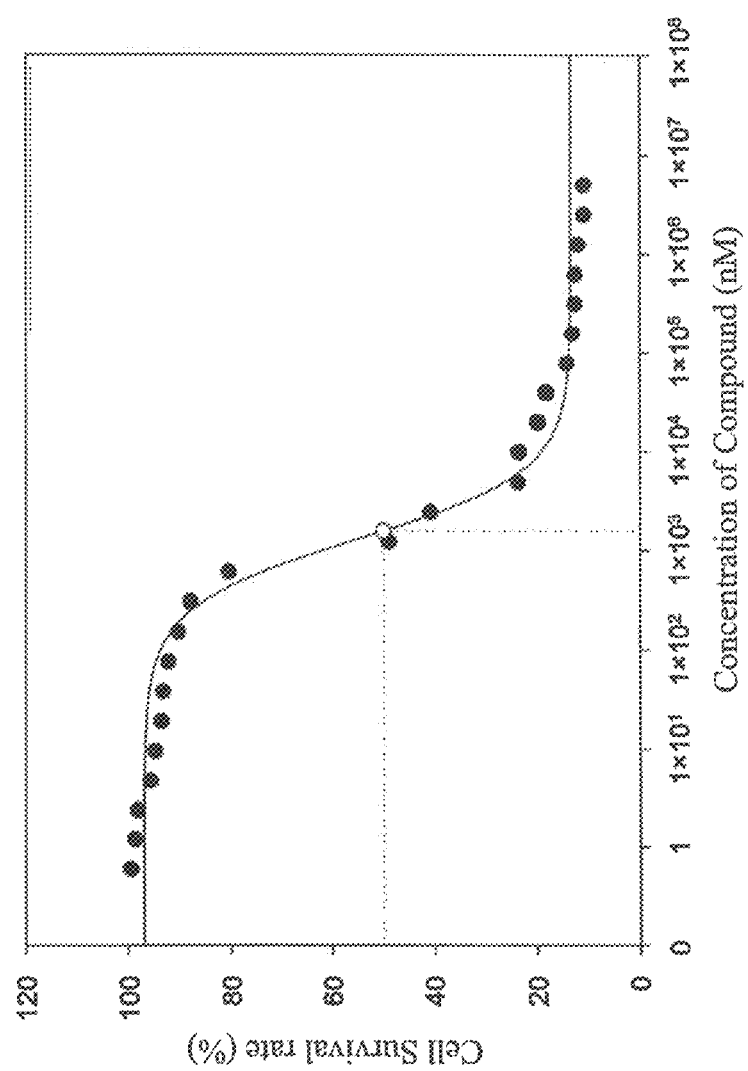

FIG. 1 shows the number of the protein kinases, out of 40 types of protein kinases, inhibited by 9 type-S protein kinase inhibitors; among the 40 types of protein kinases in the test, the selectivities for inhibiting protein kinases by the 9 type-S protein kinase inhibitors all increased, for example, compound 2 of the present invention only inhibited protein kinase CAMK2D (with an $IC_{50}$ value of less than 500 nM), as compared with STU; and FIG. 2 shows a cellular test using the type-S protein kinase inhibitors; compound 4 of the present invention in the test had an inhibitory effect on gastric cancer cell line MKN-45. The result showed that the $IC_{50}$ value was 1.6 µM.

DETAILED DESCRIPTION OF THE PREFERRED EMBODIMENTS

The following specific embodiments are used to illustrate the detailed description of the present invention, such that a person skilled in the art may readily conceive the advantages and effects of the present invention from the disclosure of the present specification. The present invention may also be implemented or applied by other different ways of implementation. Each of the details of the present disclosure may be modified and altered without departing from the spirit of the present invention, based on different aspects and applications.

Examples of "alkyl" include linear or branched $C_{1-4}$ alkyl, for example, methyl, ethyl, propyl, isopropyl, butyl, isobutyl, sec-butyl, tert-butyl, and the like.

Examples of "aryl" include $C_{6-18}$ aryl (preferably $C_{6-10}$ aryl), for example, phenyl, naphthyl (i.e., 1-naphthyl, 2-naphthyl), and the like. A preferred example is phenyl.

Examples of "$C_{5-10}$ arylheterocyclyl" include furyl, thiophenyl, pyrrolyl, pyrazolyl, imidazolyl, triazolyl (i.e., 1,2,3-triazolyl, 1,2,4-triazolyl), tetrazolyl, isoxazolyl, oxazolyl, furazanyl, isothiazolyl, thiazolyl, pyridyl (i.e., 2-pyridyl, 3-pyridyl, 4-pyridyl), pyridazinyl, pyrimidinyl, pyrazinyl, benzofuryl, isobenzofuryl, benzo[b]thiophenyl, benzo[c]thiophenyl, indolyl, isoindolyl, indolizidinyl, indazolyl, benzimidazolyl, benzotriazolyl, benzoxazinyl, 1,2-benzisoxazinyl, benzothiazolyl, 1,2-benzisothiazolyl, purinyl, quinolyl, isoquinolyl, quinolizinyl, cinnolinyl, quinazolinyl, quinoxalinyl, phthalazinyl, naphthyridinyl, pteridinyl, and the like. Preferred examples include pyrrolyl, imidazolyl, oxazinyl, triazinyl (i.e., 1,2,3-triazinyl, 1,2,4-triazinyl), tetraazinyl, pyridyl (i.e., 2-pyridyl, 3-pyridyl, 4-pyridyl), benzimidazolyl, and the like.

The present invention provides a compound of formula (I) or the salt thereof:

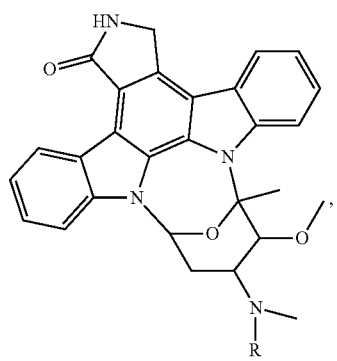

(I)

wherein R is at least one selected from the group consisting of unsubstituted $C_{1-4}$ alkyl, $C_{1-4}$ alkyl substituted by $C_{6-18}$ aryl or —$OR^1$, and —C(=O)Z;

$R^1$ is at least one selected from the group consisting of hydrogen, $C_{1-4}$ alkyl and

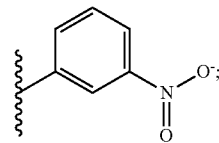

wherein Z is —C($NH_2$)$CR^2$; and $R^2$ is at least one selected from the group consisting of unsubstituted phenyl, phenyl substituted by hydroxyl or $C_{1-4}$ alkoxyl, unsubstituted $C_{5-10}$ cycloheteroaryl, $C_{5-10}$ cycloheteroaryl substituted by $C_{1-4}$ alkoxycarbonyl, carboxyl, and an ester group.

According to an embodiment of the present invention, the $C_{6-18}$ aryl is bis(biphenyl).

According to an embodiment of the present invention, the $C_{1-4}$ alkoxyl is tert-butyl.

According to an embodiment of the present invention, the $C_{1-4}$ alkoxycarbonyl is tert-butoxycarbonyl.

According to an embodiment of the present invention, the $C_{5-10}$ cycloheteroaryl is indazolyl or isoindolyl.

According to an embodiment of the present invention, R is selected from the group consisting of the followings:

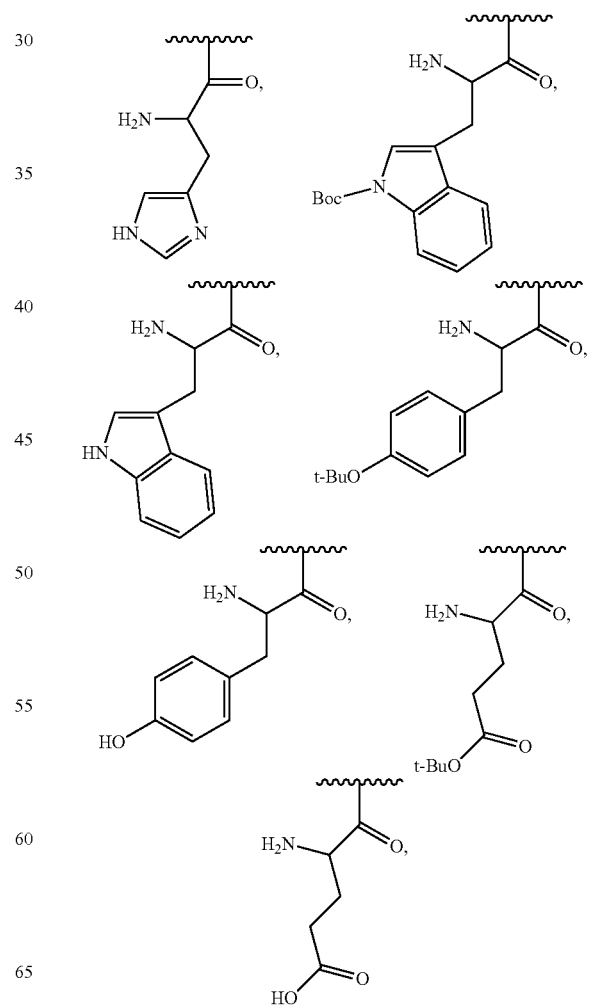

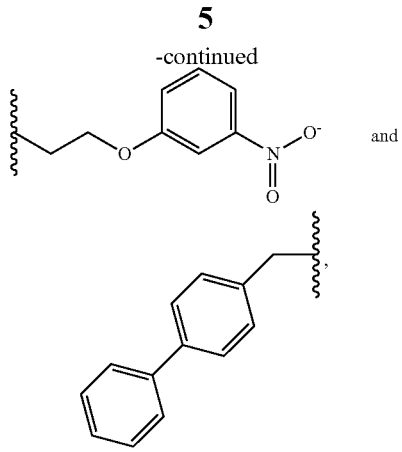

and wherein Boc is tert-butoxycarbonyl, and t-Boc is tert-butoxyl.

According to an embodiment of the present invention, the compound is a type-S protein kinase inhibitor, which binds to an ATP-binding site and a substrate-recognition site of the protein kinase, so as to inhibit the protein kinase.

According to an embodiment of the present invention, the target of type-S protein kinase inhibitors is at least one selected from the group consisting of LIMK1, ALK, PDPK1, AURKA, LCK, RET, PIM1, DYRK1A, MERTK, DAPK1, CHEK2, IRAK4, JAK2, GSK3B, CAMK2D, AKT1, PAK4, CLK1, BTK, KDR, FGFR1, CDK2, STKI1, ABL1, GSG2, MAP2K1, OXSR1, MAP3K7, AXL, PRKACA, INSR, SRPK1, EGFR, MAPKAPK2, PLK1, STK16, RPS6KB1, STK4, FGFR2 and RPS6KA5.

According to an embodiment of the present invention, the compound of the present invention or a salt thereof is used for the inhibition of the growth of cancer cells.

According to an embodiment of the present invention, the $IC_{50}$ value of the compound of the present invention or a salt thereof for the inhibition of gastric cancer cells is from 1.0 µM to 2.0 µM.

The present invention further provides a pharmaceutical composition, which includes a compound of formula (I) or a salt and a pharmaceutically acceptable carrier thereof. According to an embodiment of the present invention, the compound is a type-S protein kinase inhibitor for the treatment of cancer. The cancer is gastric cancer.

The present invention provides a use of a compound of formula (I) of the present invention or a salt thereof, which is to manufacture a protein kinase inhibitor as a drug. According to an embodiment of the present invention, the protein kinase inhibitor is a type-S protein kinase inhibitor.

The term "type-S protein kinase inhibitor" used herein refers to an inhibitor which occupies a substrate-recognition site and an ATP-binding site of a protein kinase at the same time.

The term "R group" used herein refers to the use of STU as a core framework, in which an R group is attached to an N-substituent position.

The term "R group" used herein refers to the longest linear distance from the first attached atom to any other atom of the R group in a three-dimensional structure. The measurement is performed by using a three-dimensional structure of a compound generated by using the software, openbabel (openbabel: http://openbabel.org/wiki/Main_Page; swiss pdb viewer: http://sdbv.vital-it.ch/), and then using swiss pdb viewer to calculate the longest linear distance from the first attached atom to any other atom of the R group.

The type-S protein kinase inhibitor proposed by the present invention has a high selectivity, because it can bind to an ATP-binding site and a substrate-recognition site of a protein kinase simultaneously. Said selectivity is higher than those of the inhibitors occupying only the ATP-binding sites. Nine type-S protein kinase inhibitors are designed and synthesized in the present invention, each of which uses STU as a core framework, having an attached functional group mimicking the physicochemical properties of the protein kinase substrates and with a specifically designed molecular length. As a result, each of the type-S protein kinase inhibitors can occupy an ATP-binding site and a substrate-recognition site of a protein kinase simultaneously, such that the effect of a high selectivity for inhibiting the protein kinase is achieved.

According to an embodiment of the present invention, the 9 type-S protein kinase inhibitors all substantially increase the selectivities for protein kinases. Among the 40 types of tested protein kinases, compound 2 of the present invention can inhibit one type of protein kinases (2.5%), compound 4 of the present invention can inhibit 11 types of protein kinases (27.5%), and compound 3 of the present invention can inhibit 12 types of protein kinases (30%), whereas STU can inhibit up to 39 types of protein kinases (97.5%). Moreover, compound 4 of the present invention can inhibit the growth of gastric cancer cell line MKN-45 with the $IC_{50}$ value of 1.6 µM. As shown in the results, the type-S protein kinase inhibitors have high selectivities, such that they are effective in the inhibition of the growths of tumor cell lines.

The present invention further provides a pharmaceutical composition, which includes a compound of formula (I) or a salt or a pharmaceutically acceptable carrier thereof.

The compound of the present invention has low toxicity, and may be mixed with other pharmacologically acceptable carriers to form a pharmaceutical composition for use in mammals (such as human, mice, rats, rabbits, dogs, cats, cows, horses, pigs and monkeys).

Various organic or inorganic carrier substances, which are conventionally used as materials for formulations, are used as pharmaceutically acceptable carriers. The substances are combined to form an excipient, a lubricant, a binder and a disintegrating agent for use in a solid formulation; a solvent, a solubilizing agent, a suspending agent, an isotonic agent, a buffering agent, a soothing agent, and the like, for use in a liquid formulation; and an optionally added additive (e.g., a preservative, an antioxidant, a colorant, a sweetener, and the like) for a formulation.

Examples of the dosage forms of the pharmaceutical composition include oral delivery forms (for example, tablets (including sugar-coated tablets, film-coated tablets, sublingual tablets, and orally-disintegrating tablets)), capsules (including soft capsules and microcapsules), particles, powder, disk-shaped tablets, syrup, emulsions, suspensions, thin-film (for example, orally-disintegrating thin-film), and the like; and parenteral reagents (for example, injections (for example, subcutaneous injections, intravenous injections, intramuscular injections, intraperitoneal injections, drip injections)), pills, nasal delivery forms, lung delivery forms (inhalants), and the like.

The present invention further provides a use of the compound of formula (I) above or a salt thereof, which is to manufacture a type-S protein kinase inhibitor as a drug.

The present invention will be further illustrated by the following examples. However, it should be understood that the examples are merely used for illustration, and not be construed as limiting the implementations of the present invention.

Example 1 Design and Synthesis of a Type-S Protein Kinase Inhibitor

First, STU was used as a core framework, and the length of a functional group (i.e., R group) attached to the STU was limited to from 5 to 12 Å, based on the physicochemical properties of various protein kinase substrates. Nine type-S protein kinase inhibitors, including compounds 1 to 9 of the present invention, were designed. Each of the type-S protein kinase inhibitors can bind to an ATP-binding site and a substrate-recognition site of a protein kinase simultaneously, so as to achieve the effect of selectively inhibiting the protein kinase.

I. Synthesis of Compound 1:
1. Synthesis of STU-[Fmoc-His(Trt)-OH] Compound:

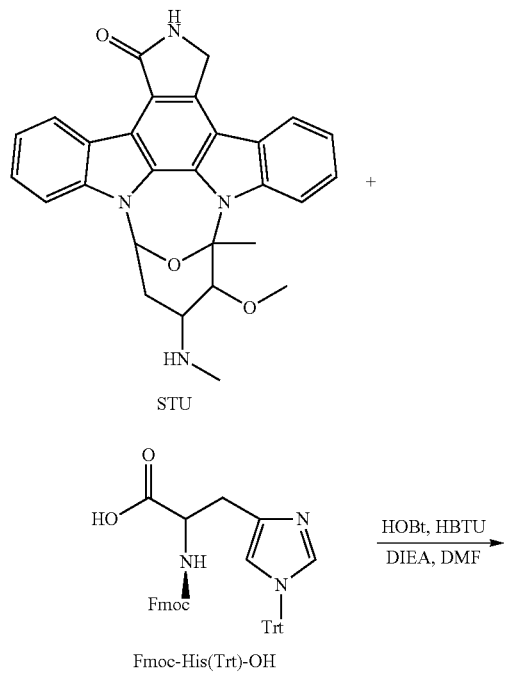

In an ice bath, 50 milligrams (mg) (0.11 millimoles (mmol)) of STU and 99.6 mg (0.16 mmol) of histidine (hereinafter abbreviated as Fmoc-His(Trt)-OH) were dissolved in 2 milliliters (ml) of a dimethylformamide (hereinafter abbreviated as DMF) solution, 78 microliters (μl) of N,N-diisopropylethylamine (hereinafter abbreviated as DIEA) was added, and then 36.5 mg (0.27 mmol) of 1-hydroxybenzotriazole hydrate (hereinafter abbreviated as HOBt) and 106 mg (0.27 mmol) of O-benzotriazole-N,N, N',N',-tetramethyl-uronium-hexafluorophosphate (hereinafter abbreviated as HBTU) were added to obtain a reactant. The reactant reacted for 30 minutes in the ice bath, and then it was transferred to room temperature for a continuing reaction for 22 hours. A vacuum system was used to remove the solvent from the reactant, and a crude product was obtained. Then, a high-performance liquid chromatograph was for purification, and 21 mg of STU-[Fmoc-His(Trt)-OH] was obtained. Yield: 18%.

The analytical conditions for the high-performance liquid chromatograph were dissolving the crude product, STU-[Fmoc-His(Trt)-OH], in double-distilled water, using a Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elution for 10 minutes. A single absorption peak was found at the retention time of about 18.42 minutes. The absorption peak indicated STU-[Fmoc-His(Trt)-OH]. ESI-MS (m/z): calculated value: 1067.44, and measured value: 1068.8 [M+H]$^+$.

2. Synthesis of Compound 1:

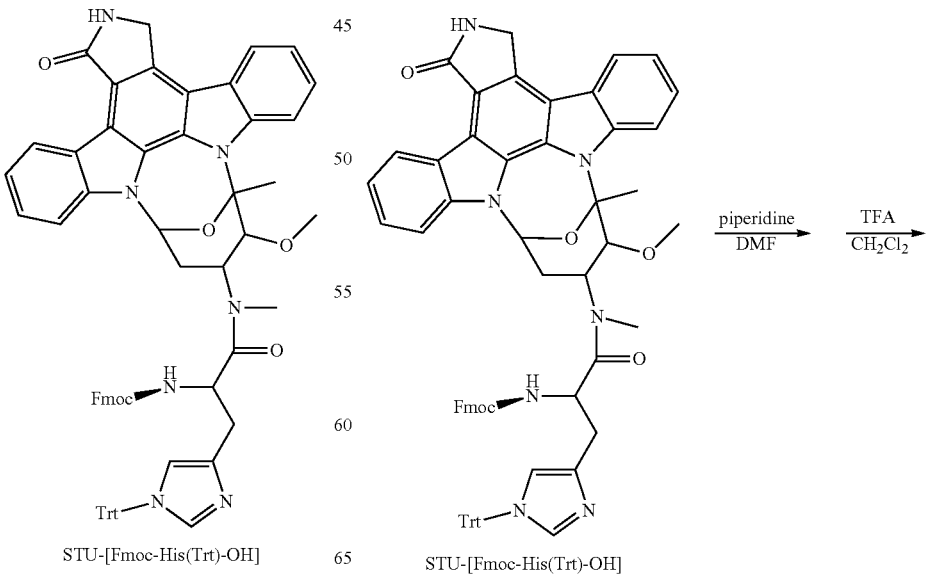

II. Syntheses of Compounds 2 and 3

1. Synthesis of STU-[Fmoc-Trp(Boc)-OH] Compound:

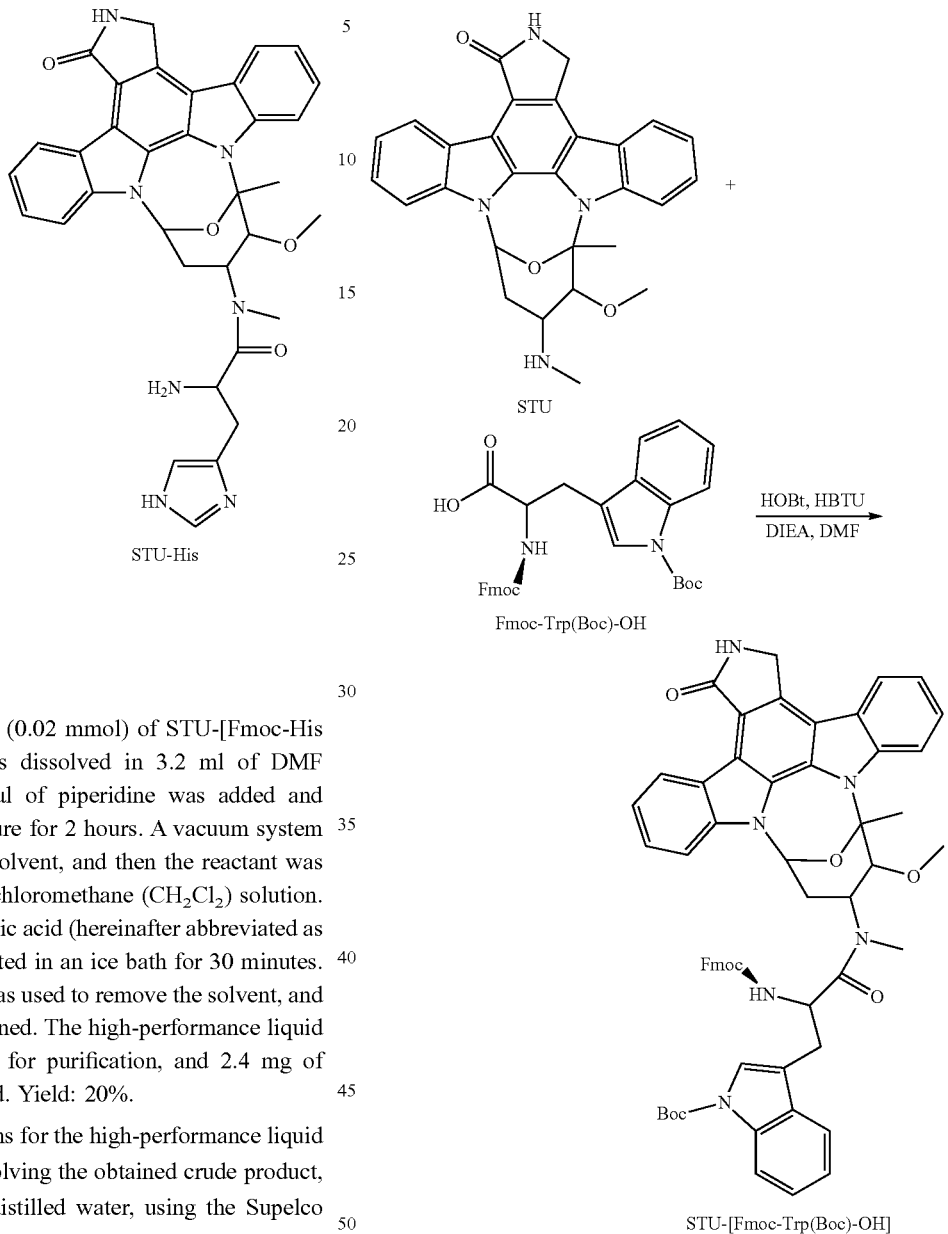

Twenty-one milligrams (0.02 mmol) of STU-[Fmoc-His(Trt)-OH] compound was dissolved in 3.2 ml of DMF solution, and then 640 μl of piperidine was added and reacted at room temperature for 2 hours. A vacuum system was used to remove the solvent, and then the reactant was dissolved in 2 ml of a dichloromethane ($CH_2Cl_2$) solution. Then, 1 ml of trifluoroacetic acid (hereinafter abbreviated as TFA) was added and reacted in an ice bath for 30 minutes. Then, a vacuum system was used to remove the solvent, and a crude product was obtained. The high-performance liquid chromatograph was used for purification, and 2.4 mg of compound 1 was obtained. Yield: 20%.

The analytical conditions for the high-performance liquid chromatograph were dissolving the obtained crude product, compound 1, in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% of formic acid (solution A) and methanol containing 0.1% of formic acid (solution B). The flow rate was 1 ml/min. Fifty percents of solution B was used for elution for 5 minutes, a gradient of 50% to 100% of solution B was used for elution for 10 minutes, and then 100% of solution B was used for continual elution for 10 minutes. A single absorption peak was found at the retention time of about 7.53 minutes. The absorption peak indicated compound 1. ESI-MS (m/z): calculated value: 603.26, and measured value: 604.0 $[M+H]^+$.

Twenty milligrams (0.04 mmol) of STU and 34 mg (0.06 mmol) of Fmoc-Trp(Boc)-OH were dissolved in 2 ml of DMF solution, 31.2 μl of DIEA was added, and then 14.4 mg (0.10 mmol) of HOBt and 42.4 mg (0.105 mmol) of HBTU were added to obtain a reactant. The reactant reacted in an ice bath for 30 minutes, and it was then transferred to room temperature for a continuing reaction for 22 hours. A vacuum system was used to remove the solvent, and a crude product was obtained. The high-performance liquid chromatograph was used for purification, and 20 mg of STU-[Fmoc-Trp(Boc)-OH] compound was obtained. Yield: 48%.

The analytical conditions for the high-performance liquid chromatograph were dissolving the crude product, STU-[Fmoc-Trp(Boc)-OH], in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% of formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for elution for 10 minutes. A single absorption peak was found at the retention time of about 19.27 minutes. The absorption peak indicated STU-[Fmoc-Trp(Boc)-OH]. ESI-MS (m/z): calculated value: 974.4, and measured value: 975.5 [M+H]$^+$.

2. Synthesis of Compound 2:

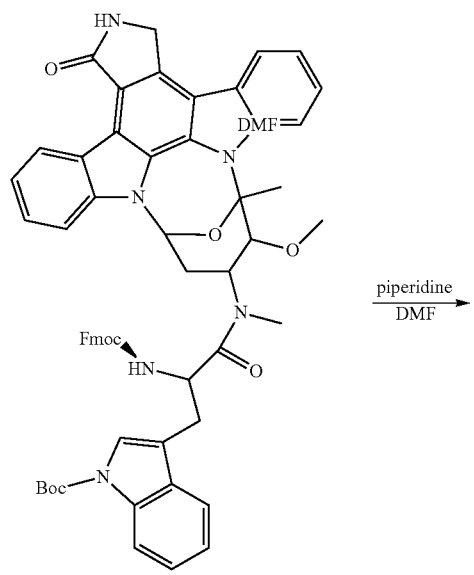

Twenty milligrams (0.02 mmol) of STU-[Fmoc-Trp(Boc)-OH] compound was dissolved in 2 ml of DMF solution, and then 400 μl of piperidine was added and reacted at room temperature for 2 hours. A vacuum system was used to remove the solvent, and a crude product was obtained. The high-performance liquid chromatograph was used for purification, and 9.7 mg of compound 2 was obtained. Yield: 64%.

The analytical conditions for the high-performance liquid chromatograph were dissolving the crude product, compound 2, in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% of formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elusion for 10 minutes. A single absorption peak was found at the retention time of about 16.68 minutes. The absorption peak indicated compound 2. ESI-MS (m/z): calculated value: 752.3, and measured value: 753.3 [M+H]$^+$.

3. Synthesis of Compound 3:

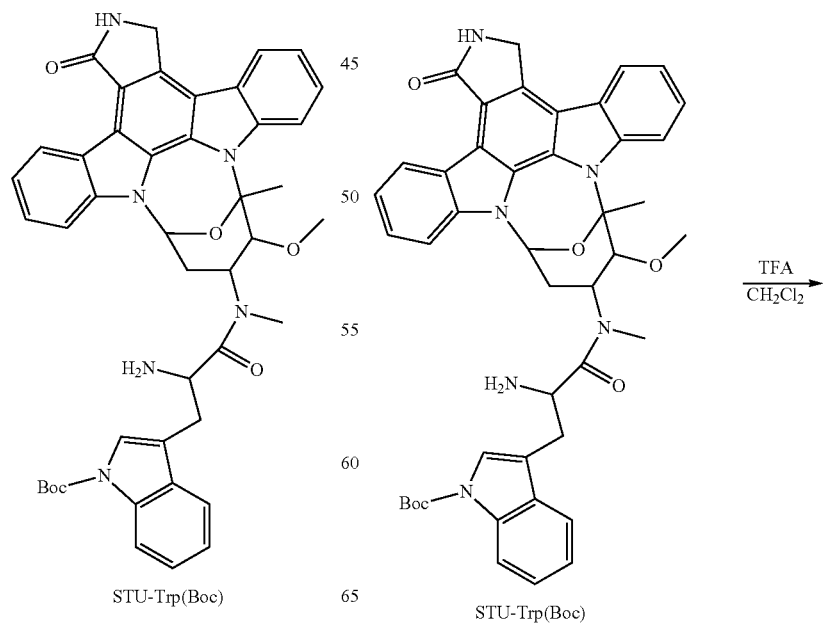

III. Syntheses of Compounds 4 and 5:
1. Synthesis of STU-[Fmoc-Tyr(OtBu)-OH] Compound:

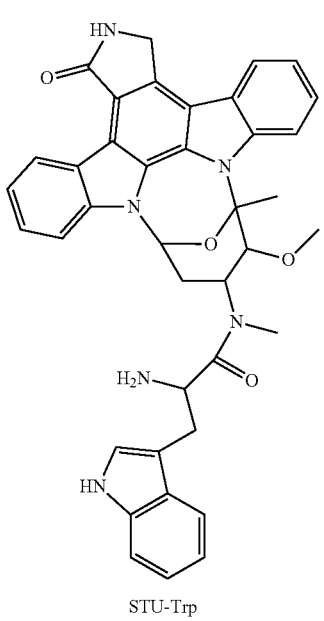

STU-Trp

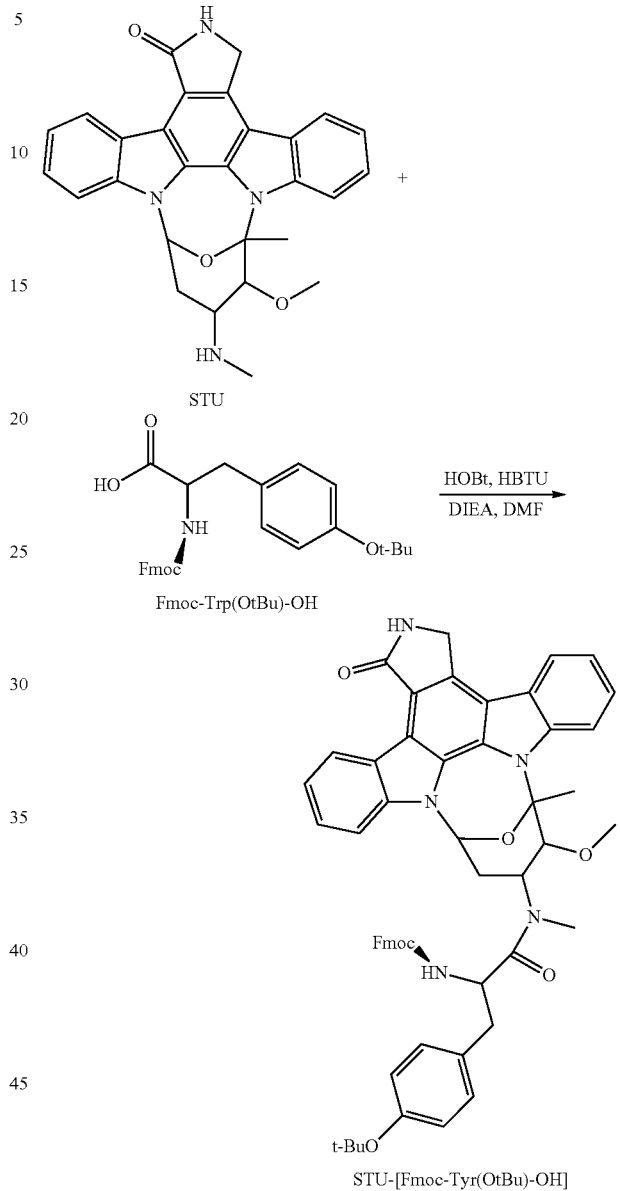

Seven milligrams (0.01 mmol) of compound 2 was dissolved in 1 ml of the dichloromethane solution, and then 1 ml of trifluoroacetic acid was added and reacted for 30 minutes in an ice bath. A vacuum system was used to remove the solvent, and a crude product was obtained. The high-performance liquid chromatograph was used for purification, and 2.4 mg of compound 3 was obtained. Yield: 37%.

The analytical conditions for the high-performance liquid chromatograph were dissolving the crude product, compound 3, in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elution for 10 minutes. A single absorption peak was found at the retention time of about 14.35 minutes. The absorption peak indicated compound 3. ESI-MS (m/z): calculated value: 652.3, and measured value: 651.2 [M+H]$^+$.

Twenty milligrams (0.04 mmol) of STU and 29.6 mg (0.06 mmol) of Fmoc-Tyr(OtBu)-OH were dissolved in 2 ml of DMF solution, 31.2 μl of DIEA was added, and then 14.4 mg (0.10 mmol) of HOBt and 42.4 mg (0.105 mmol) of HBTU were added to obtain a reactant. The reactant reacted for 30 minutes in the ice bath, and was then transferred to room temperature for a continuing reaction for 22 hours. A vacuum system was used to remove the solvent, and a crude product was obtained. The high-performance liquid chromatograph was used for purification, and 24.1 mg of STU-[Fmoc-Tyr(OtBu)-OH] compound was obtained. Yield: 62%.

The analytical conditions for the high-performance liquid chromatograph were dissolving the crude product, STU-[Fmoc-Tyr(OtBu)-OH], in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for a continual elution for 10 minutes. A single absorption peak was found at the retention time of about 18.65 minutes. The absorption peak indicated STU-[Fmoc-Tyr(OtBu)-OH]. ESI-MS (m/z): calculated value: 907.4, and measured value: 908.5 [M+H]⁺.

2. Synthesis of Compound 4:

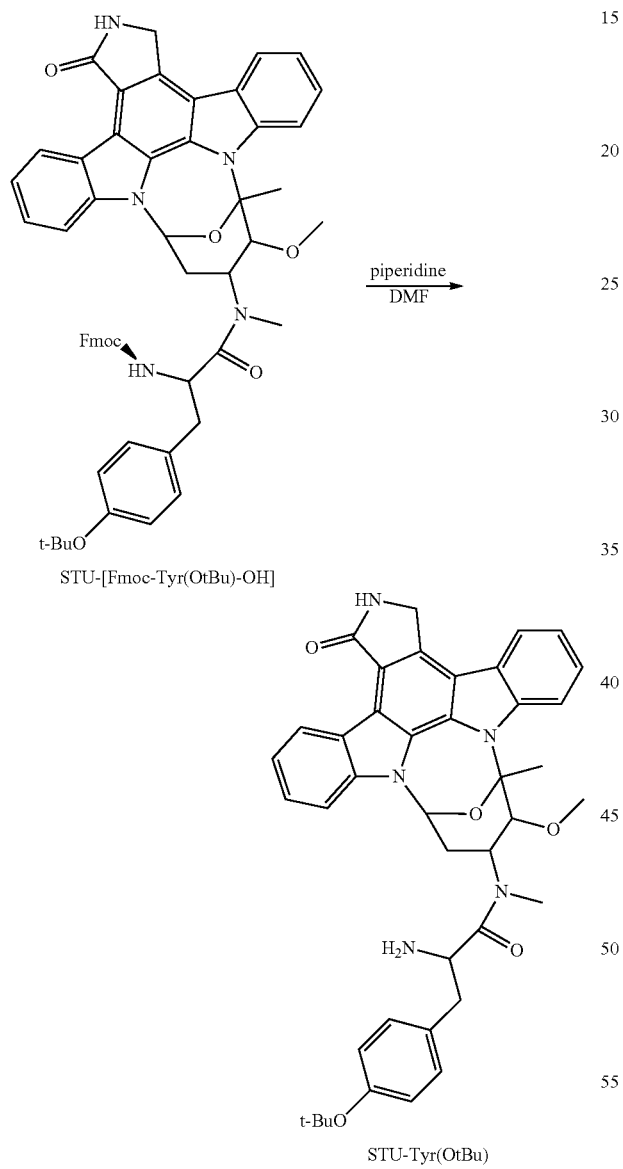

Twenty-four milligrams (0.026 mmol) of STU-[Fmoc-Tyr(OtBu)-OH] compound was dissolved in 2 ml of DMF solution, and then 400 μl of piperidine was added and reacted at room temperature for 2 hours. A vacuum system was used to remove the solvent, and a crude product was obtained. The high-performance liquid chromatograph was used for purification, and 12.6 mg of compound 4 was obtained. Yield: 71%.

The analytical conditions for the high-performance liquid chromatograph were dissolving the obtained crude product, compound 4, in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for a continual elution for 10 minutes. A single absorption peak was found at the retention time of about 14.70 minutes. The absorption peak indicated compound 4. ESI-MS (m/z): calculated value: 685.3, and measured value: 686.5 [M+H]⁺.

3. Synthesis of Compound 5:

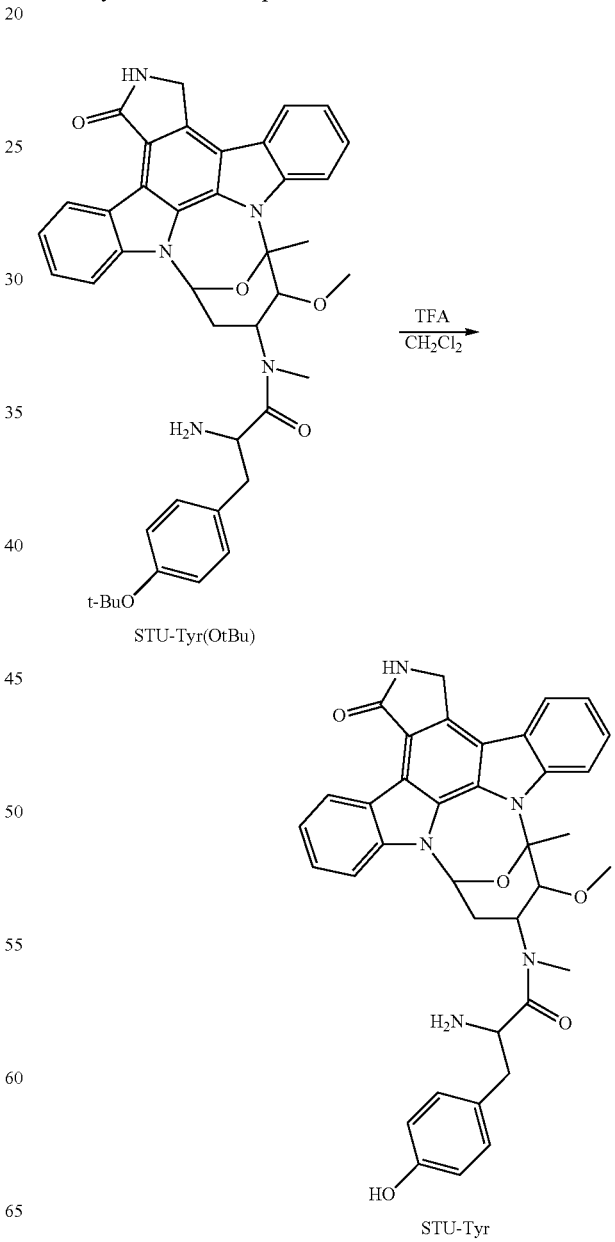

Nine milligrams (0.013 mmol) of compound 4 was dissolved in 1 ml of dichloromethane solution, and then 1 ml of trifluoroacetic acid was added and reacted for 30 minutes in an ice bath. A vacuum system was used to remove the solvent, and a crude product was obtained. The high-performance liquid chromatograph was used for purification, and 5.2 mg of compound 5 was obtained. Yield: 62%.

The analytical conditions for the high-performance liquid chromatograph were dissolving the obtained crude product, compound 5, in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for a continual elution for 10 minutes. A single absorption peak was found at the retention time of about 7.64 minutes. The absorption peak indicated compound 5. ESI-MS (m/z): calculated value: 629.3, and measured value: 630.1 [M+H]$^+$.

IV. Syntheses of Compounds 6 and 7:
1. Synthesis of STU-[Fmoc-Glu(OtBu)-OH] Compound:

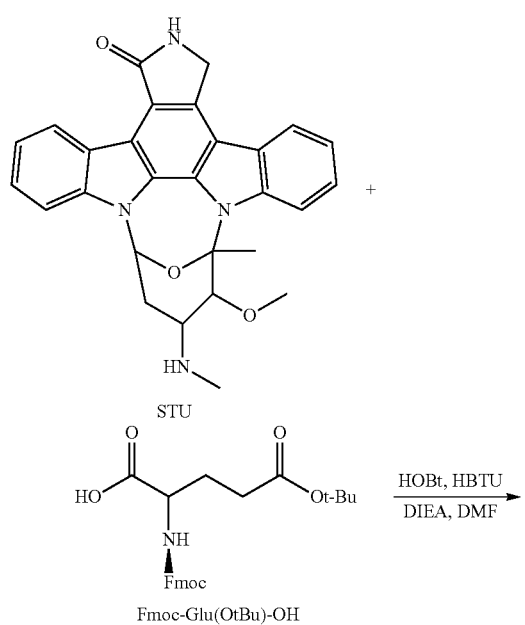

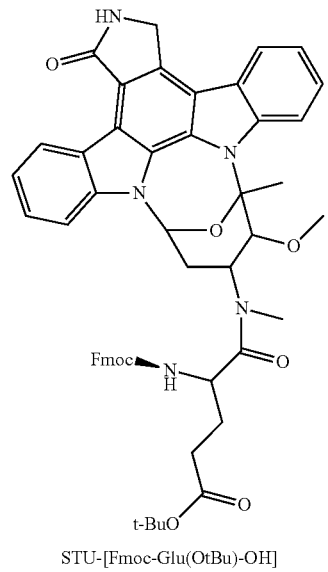

STU-[Fmoc-Glu(OtBu)-OH]

Thirty milligrams (0.064 mmol) of STU and 41 mg (0.10 mmol) of Fmoc-Glu(OtBu)-OH were dissolved in 2 ml of DMF solution, 46.8 μl of DIEA was added, and then 21.9 mg (0.10 mmol) of HOBt and 61.2 mg (0.105 mmol) of HBTU were added to obtain a reactant. The reactant reacted for 30 minutes in the ice bath, and was then transferred to room temperature for a continuing reaction for 22 hours. A vacuum system was used to remove the solvent, and a crude product was obtained. The high-performance liquid chromatograph was used for purification, and 20.3 mg of STU-[Fmoc-Glu(OtBu)-OH] was obtained. Yield: 36%.

The analytical conditions for the high-performance liquid chromatograph were dissolving the crude product, STU-[Fmoc-Glu(OtBu)-OH], in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for a continual elution for 10 minutes. A single absorption peak was found at the retention time of about 18.26 minutes. The absorption peak was STU-[Fmoc-Glu(OtBu)-OH] compound. ESI-MS (m/z): calculated value: 873.4, and measured value: 874.3 [M+H]$^+$.

2. Synthesis of Compound 6:

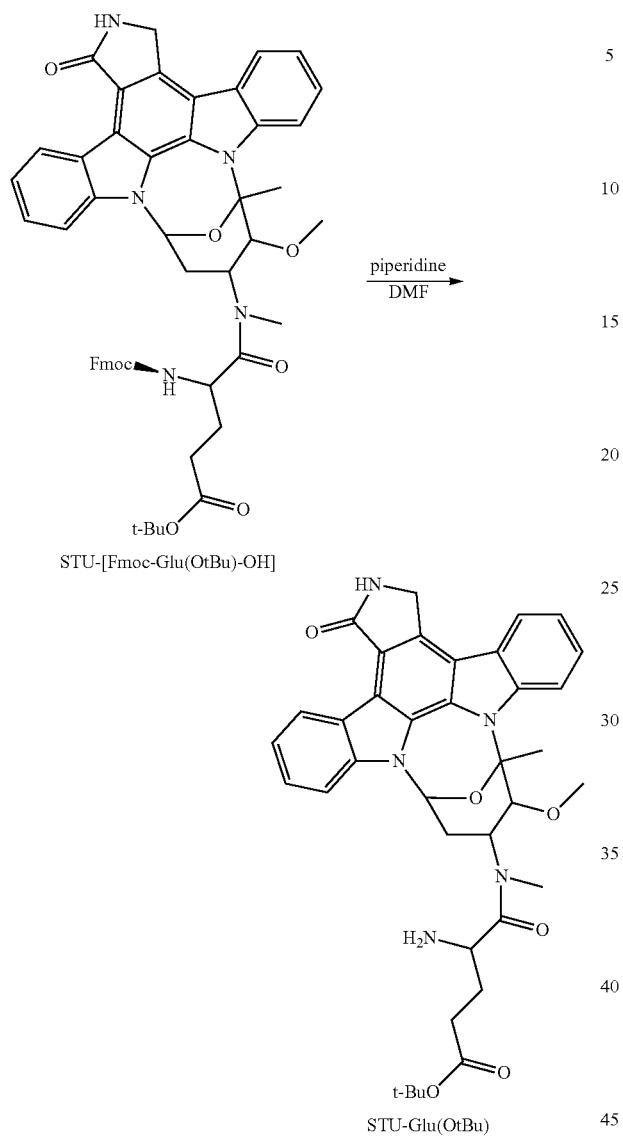

STU-[Fmoc-Glu(OtBu)-OH]

piperidine / DMF →

STU-Glu(OtBu)

Twenty milligrams (0.023 mmol) of STU-[Fmoc-Glu(OtBu)-OH] compound was dissolved in 2 ml of DMF solution, and then 400 µl of piperidine was added and reacted at room temperature for 2 hours. A vacuum system was used to remove the solvent, and a crude product was obtained. The high-performance liquid chromatograph was used for purification, and 10.1 mg of compound 6 was obtained. Yield: 67%.

The analytical conditions for the high-performance liquid chromatograph were dissolving the obtained crude product, compound 6, in double-distilled water, using the Supelco RP-C18 column (5 µm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elution for 10 minutes. A single absorption peak was found at the retention time of about 14.38 minutes. The absorption peak indicated compound 6. ESI-MS (m/z): calculated value: 651.3, and measured value: 652.2 [M+H]$^+$.

3. Synthesis of Compound 7:

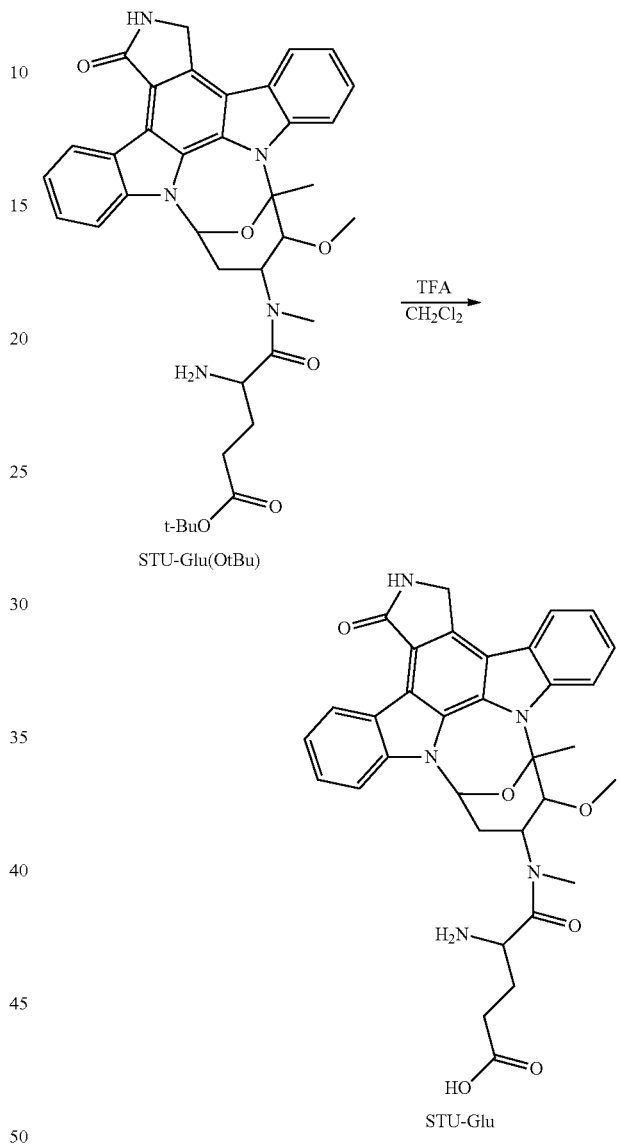

STU-Glu(OtBu)

TFA / CH$_2$Cl$_2$ →

STU-Glu

Six point five milligrams (0.01 mmol) of compound 6 was dissolved in 1 ml of dichloromethane solution, and then 1 ml of trifluoroacetic acid was added and reacted for 30 minutes in an ice bath. A vacuum system was used for removing the solvent, and a crude product was obtained. The high-performance liquid chromatograph was used for purification, and 2 mg of compound 7 was obtained. Yield: 33.6%.

The analytical conditions for the high-performance liquid chromatograph were dissolving the obtained crude product, compound 7, in double-distilled water, using the Supelco RP-C18 column (5 µm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elution for 10 minutes. A single absorption peak was found at the retention time of about 6.13 minutes. The absorption peak indicated compound 7. ESI-MS (m/z): calculated value: 595.2, and measured value: 596.0 [M+H]$^+$.

V. Synthesis of Compound 8:

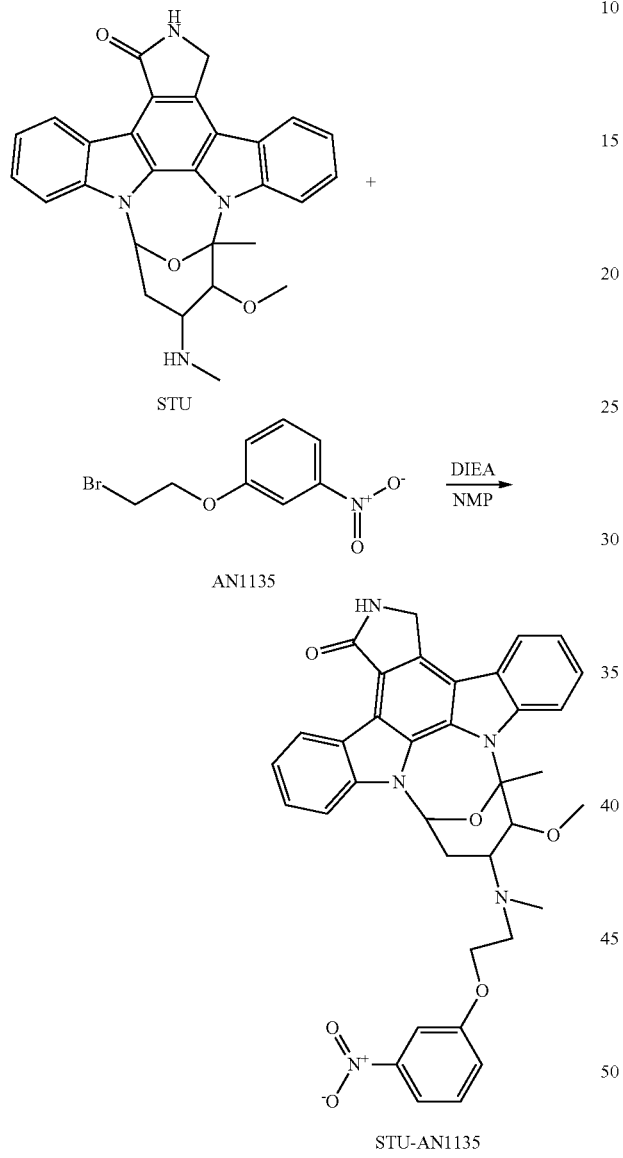

Thirty-nine point one milligrams (0.083 mmol) of STU was dissolved in 300 μl of an N-methylpyrrolidinone (hereinafter abbreviated as NMP) solution, and 53 μl of DIEA and 70.3 mg (0.029 mmol) of 1-(2-bromoethoxy)-3-nitrobenzene (hereinafter abbreviated AN1135) to obtain a reactant. The reactant reacted at 40° C. for 108 hours. After the reaction, dichloromethane and water were used for extraction, and an organic phase was collected. Then, the high-performance liquid chromatograph was used for purification. Then, elution was performed with dichloromethane and methanol at a ratio of 20:1. After collecting the eluent, it was dried by concentrating under a reduced pressure, and 24.5 mg of compound 8 was obtained. Yield: 47%.

The analytical conditions for the high-performance liquid chromatograph were dissolving the obtained compound 8 in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% solution B was used for elution for 7.5 minutes, and then 100% of solution B was used for continual elution for 10 minutes. A single absorption peak was found at the retention time of about 12.41 minutes. The absorption peak indicated compound 8. ESI-MS (m/z): calculated value: 631.5, and measured value: 632.2 [M+H]$^+$.

VI. Synthesis of Compound 9:

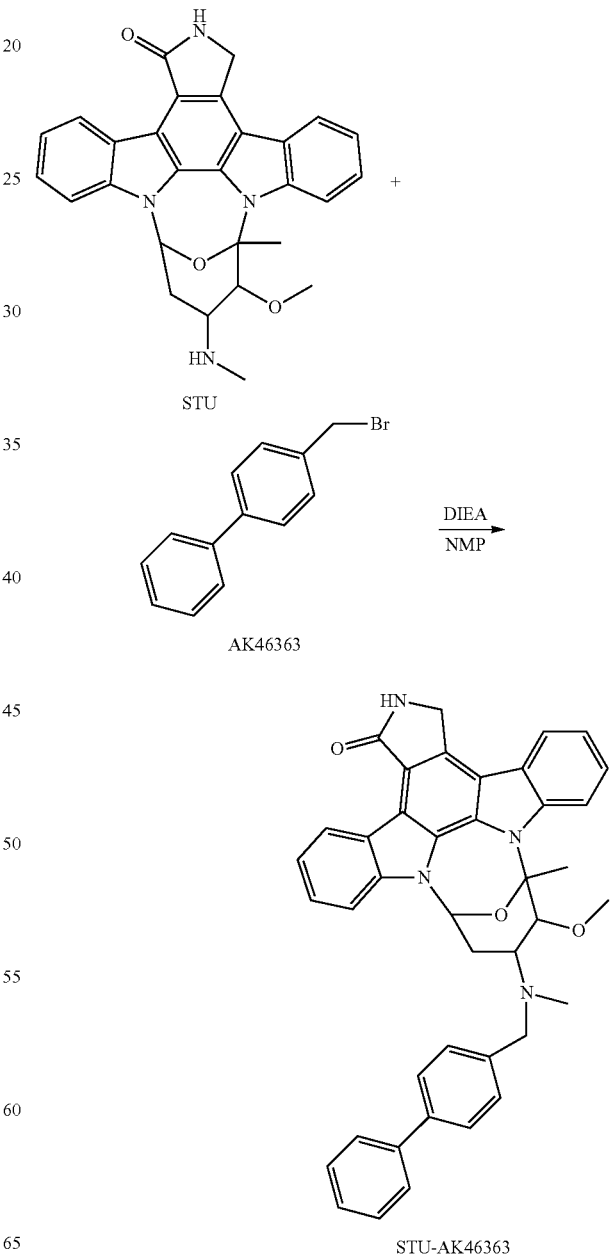

Thirty-seven point nine milligrams (0.081 mmol) of STU was dissolved in 500 μl of NMP solution, and 27 μl of DIEA and 29.5 mg (0.12 mmol) of 4-bromomethyl-1,1'-biphenyl (hereinafter abbreviated as AK46363) to obtain a reactant. The reactant reacted at room temperature for 24 hours. After the reaction, dichloromethane and water was used for extraction, and an organic phase was collected. Then, the high-performance liquid chromatograph was used for purification. Then, elution was performed with dichloromethane and methanol at a ratio of 20:1. After collecting the eluent, it was dried by concentrating under a reduced pressure, and 12.8 mg of compound 9 was obtained. Yield: 25%.

The analytical conditions for the high-performance liquid chromatograph were dissolving the obtained compound 9 in double-distilled water, using the Supelco RP-C18 column (5 μm, 4.6×250 mm) for purification, and performing UV (with wavelengths of 254 nm and 300 nm) detection. The solutions used as a mobile phase were deionized water containing 0.1% formic acid (solution A) and methanol containing 0.1% of formic acid (solution B). The flow rate was 1 ml/min. Forty percents of solution B was used for elution for 7.5 minutes, a gradient of 40% to 60% of solution B was used for elution for 7.5 minutes, and then 100% of solution B was used for continual elution for 10 minutes. A single absorption peak was found at the retention time of about 12.45 minutes. The absorption peak indicated compound 9. ESI-MS (m/z): calculated value: 632.58, and measured value: 633.2 [M+H]$^+$.

Table 1 below shows examples of the compound of formula (I) of the present invention, and summarizes the structural formulae, and the types, the lengths and molecular sizes of R groups of compounds 1-9 synthesized in the present invention.

TABLE 1

Examples of the compound of formula (I) of the present invention.

| No. | Structure | R group | Length of R group (Å) | MS (m/Z) |
|---|---|---|---|---|
| Compound 1 | 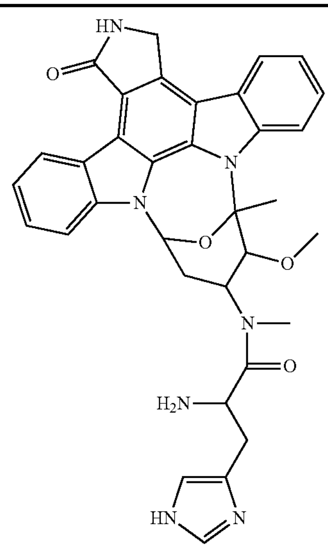 | | Length of R group 6.7 | [M + H]$^+$ = 604.0 |
| Compound 2 | 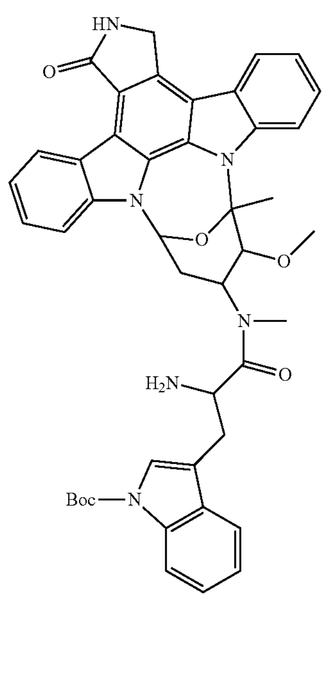 [SMILES: COC1C(N(C)C(=O)C(N)Cc2cn(C(=O)OC(C)(C)C)c3ccccc23)CC2OC1(C)n1c3ccccc3c3c4c(c5c6ccccc6n2c5c31)C(=O)NC4] | | 10.7 | [M + H]$^+$ = 753.3 |

TABLE 1-continued
Examples of the compound of formula (I) of the present invention.
| No. | Structure | R group | Length of R group (Å) | MS (m/Z) |
|---|---|---|---|---|
| Compound 3 | 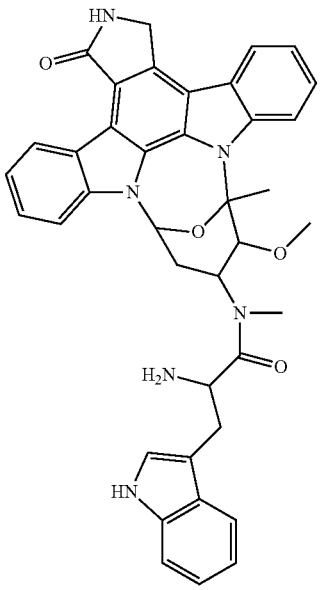 [SMILES: COC1C(N(C)C(=O)C(N)Cc2c[nH]c3ccccc23)CC2OC1(C)n1c3ccccc3c3c4c(c5c6ccccc6n2c5c31)C(=O)NC4] | 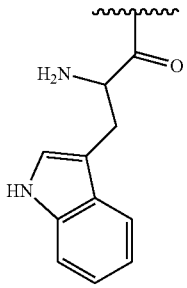 [SMILES: *C(=O)C(N)Cc1c[nH]c2ccccc12] | 8.3 | [M + H]$^+$ = 651.2 |
| Compound 4 | 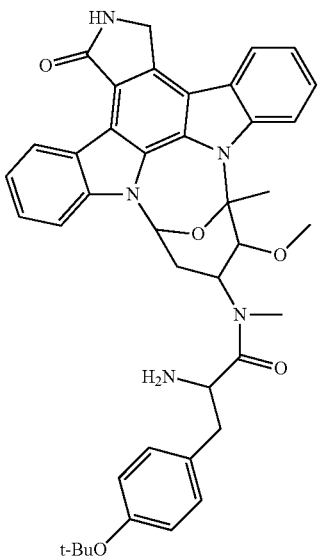 [SMILES: COC1C(N(C)C(=O)C(N)Cc2ccc(OC(C)(C)C)cc2)CC2OC1(C)n1c3ccccc3c3c4c(c5c6ccccc6n2c5c31)C(=O)NC4] | 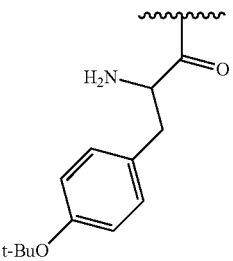 [SMILES: *C(=O)C(N)Cc1ccc(OC(C)(C)C)cc1] | 10.7 | [M + H]$^+$ = 686.5 |

TABLE 1-continued

Examples of the compound of formula (I) of the present invention.

| No. | Structure | R group | Length of R group (Å) | MS (m/Z) |
|---|---|---|---|---|
| Compound 5 | 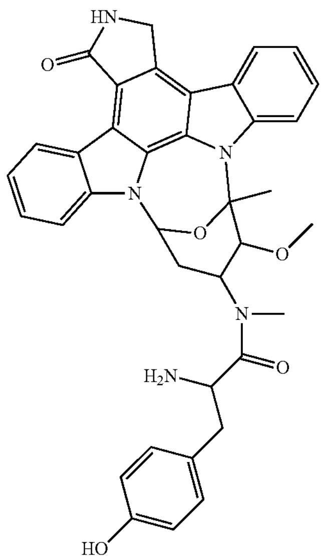 [SMILES: COC1C(N(C)C(=O)C(N)Cc2ccc(O)cc2)CC2OC1(C)n1c3ccccc3c3c4c(c5c6ccccc6n2c5c31)C(=O)NC4] | | 8.5 | $[M + H]^+ = 630.1$ |
| Compound 6 | 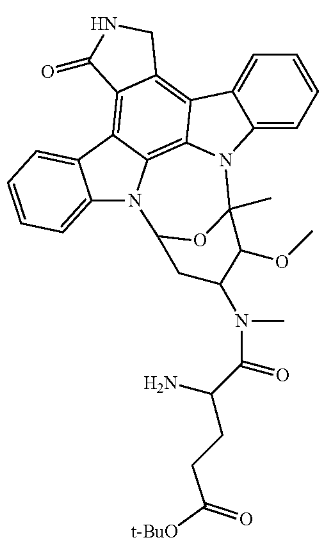 [SMILES: COC1C(N(C)C(=O)C(N)CCC(=O)OC(C)(C)C)CC2OC1(C)n1c3ccccc3c3c4c(c5c6ccccc6n2c5c31)C(=O)NC4] | | 9.3 | $[M + H]^+ = 652.2$ |

TABLE 1-continued

Examples of the compound of formula (I) of the present invention.

| No. | Structure | R group | Length of R group (Å) | MS (m/Z) |
|---|---|---|---|---|
| Compound 7 | 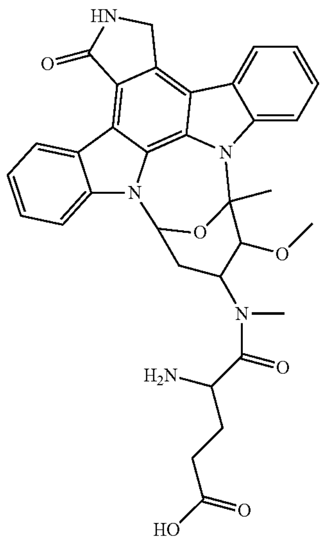 [SMILES: COC1C(N(C)C(=O)C(N)CCC(=O)O)CC2OC1(C)n1c3ccccc3c3c4c(c5c6ccccc6n2c5c31)C(=O)NC4] | | 7.0 | [M + H]⁺ = 596.0 |
| Compound 8 | 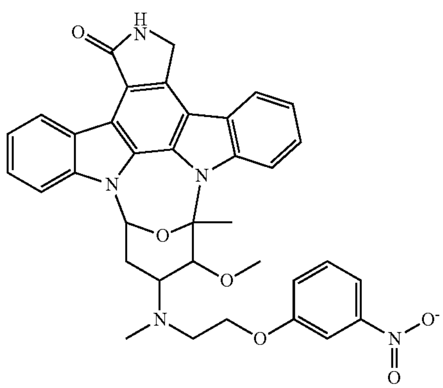 | | 9.5 | [M + H]⁺ = 632.2 |
| Compound 9 | 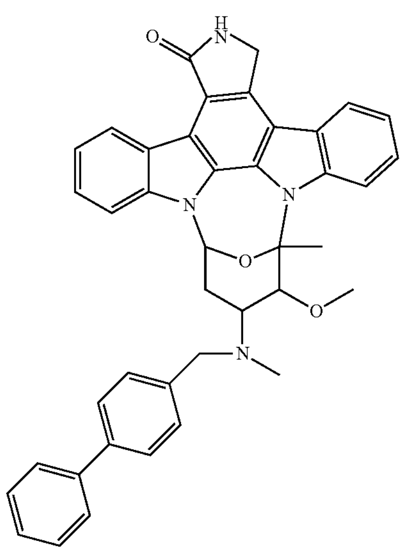 [SMILES: COC1C(N(C)Cc2ccc(-c3ccccc3)cc2)CC2OC1(C)n1c3ccccc3c3c4c(c5c6ccccc6n2c5c31)C(=O)NC4] | | 9.2 | [M + H]⁺ = 633.2 |

Example 2 Type-S Protein Kinase Inhibitors Had Selective Inhibitory Effects on Various Protein Kinases The 9 type-S protein kinase inhibitors (including compounds 1 to 9) synthesized were tested for their inhibitory effects on various protein kinases in the present invention.

First, according to the docking results of the present invention, it showed that the type-S protein kinase inhibitor can bind to the ATP-binding site and substrate-recognition site of the protein kinase simultaneously. In the results, compound 7 of the present invention can form hydrogen bonds and electrostatic forces with the positively-charged sites of the protein kinase INSR (hereinafter abbreviated as INSR) at residues K1085 and R1089. Compound 1 of the present invention can bind to the arginine residue of the substrate binding site of protein kinase AKT1 (hereinafter abbreviated as AKT1), and interact with residues E234, F236, E278 and D439 in AKT1. Compounds 2 and 8 of the present invention can interact with residues E97, F99 and E100 in protein kinase CAMK2D (hereinafter abbreviated as CAMK2D), and can also interact with residues E166, L168, R172 and E209 in protein kinase PDPK1 (hereinafter, abbreviated as PDPK1).

Kinase Profiler services provided by Research Biology Corp. (http://www.reactionbiology.com) were used to analyze the data of the 9 type-S protein kinase inhibitors against the 40 types of protein kinases. The nine type-S protein kinase inhibitors (i.e., compounds 1 to 9 of the present invention) at a concentration of 500 nM were used in the test, and the percentage of the remaining kinase activity for each of the type-S protein kinase inhibitors was used for assessing the inhibitory ability of the type-S protein kinase inhibitors. If the percentage of the residual kinase activity is less than or equal to 50%, it is considered that the type-S protein kinase inhibitor can inhibit the protein kinase. The test results showed that the type-S protein kinase inhibitors are selective inhibitors. As shown in the results in Table 2 and FIG. 1 below, compounds 2, 4 and 3 of the present invention inhibited 1, 11 and 12 types of protein kinases, respectively, and which corresponded to 2.5%, 27.5% and 30% of the 40 types of protein kinases being tested. On the contrary, STU inhibited 39 types of protein kinases, which corresponds to 97.5% of the 40 types of protein kinases being tested. Therefore, it is confirmed that the type-S protein kinase inhibitors are novel selective protein kinase inhibitors.

TABLE 2

Analytical results of the 9 type-S protein kinase inhibitors against 40 types of protein kinases

| No. | Protein Kinase | STU | Compound 1 | Compound 7 | Compound 6 | Compound 5 | Compound 4 | Compound 3 | Compound 2 | Compound 9 | Compound 8 |
|---|---|---|---|---|---|---|---|---|---|---|---|
| 1 | LIMK1 | −0.6 | 18.8 | 1.4 | 39.5 | 46.9 | 66.9 | 90.1 | 103.4 | 56.5 | 49.9 |
| 2 | ALK | −0.3 | 3.3 | 4.7 | 44.7 | 29.1 | 56.7 | 63.1 | 85.4 | 17.6 | 19.5 |
| 3 | PDPK1 | −1.8 | 0.5 | 0.5 | 3.4 | 2.0 | 13.3 | 13.9 | 81.0 | 2.7 | 4.7 |
| 4 | AURKA | 0.2 | 2.1 | 0.9 | 5.3 | 4.9 | 19.7 | 23.2 | 86.2 | 11.2 | 12.1 |
| 5 | LCK | 0.5 | 2.1 | 3.0 | 44.0 | 11.5 | 68.8 | 46.3 | 97.0 | 14.0 | 24.0 |
| 6 | RET | 0.6 | 6.0 | 1.6 | 34.2 | 21.3 | 63.0 | 53.7 | 101.4 | 14.8 | 16.2 |
| 7 | PIM1 | 0.6 | 2.4 | 2.5 | 43.0 | 3.0 | 44.2 | 21.7 | 88.9 | 21.8 | 24.6 |
| 8 | DYRK1A | 0.6 | 0.4 | 0.6 | 13.8 | 0.6 | 17.8 | 27.7 | 88.6 | 18.5 | 25.3 |
| 9 | MERTK | 1.1 | 26.7 | 40.0 | 85.2 | 69.2 | 88.1 | 83.9 | 96.8 | 52.3 | 63.1 |
| 10 | DAPK1 | 1.9 | 26.0 | 26.2 | 101.2 | 105.4 | 96.4 | 108.3 | 107.1 | 115.6 | 89.8 |
| 11 | CHEK2 | 1.6 | 30.3 | 47.2 | 82.7 | 73.2 | 80.4 | 78.2 | 95.8 | 37.7 | 46.7 |
| 12 | IRAK4 | 1.6 | 33.4 | 46.8 | 63.5 | 85.9 | 87.4 | 71.2 | 100.8 | 26.6 | 27.9 |
| 13 | JAK2 | 0.8 | 4.4 | 1.5 | 39.6 | 19.4 | 36.4 | 43.7 | 70.0 | 4.4 | 5.2 |
| 14 | GSK3B | 2.3 | 17.9 | 9.6 | 79.7 | 29.4 | 86.6 | 83.4 | 94.2 | 46.6 | 51.8 |
| 15 | CAMK2D | 0.4 | 2.0 | 2.3 | 12.7 | 10.1 | 6.7 | 16.3 | 16.1 | 1.1 | 0.3 |
| 16 | AKT1 | 3.8 | 19.6 | 31.5 | 67.5 | 66.8 | 79.6 | 90.6 | 97.6 | 46.9 | 52.3 |
| 17 | PAK4 | 4.8 | 40.2 | 38.4 | 80.8 | 53.3 | 95.2 | 101.5 | 110.3 | 91.8 | 99.9 |
| 18 | CLK1 | 4.5 | 15.9 | 32.3 | 86.6 | 29.6 | 98.6 | 83.9 | 107.4 | 73.7 | 74.8 |
| 19 | BTK | 3.6 | 13.9 | 11.9 | 43.6 | 37.8 | 65.4 | 62.8 | 90.6 | 55.8 | 53.9 |
| 20 | KDR | 3.7 | 6.5 | 5.4 | 42.4 | 16.3 | 50.8 | 50.5 | 101.6 | 43.6 | 43.3 |
| 21 | FGFR1 | 3.0 | 5.1 | 3.2 | 29.5 | 16.6 | 53.3 | 46.6 | 101.0 | 25.7 | 30.1 |
| 22 | CDK2 | 3.9 | 16.5 | 19.3 | 55.0 | 56.9 | 57.5 | 68.0 | 76.6 | 8.2 | 12.3 |
| 23 | STK11 | 9.5 | 88.7 | 79.9 | 104.3 | 101.7 | 112.7 | 105.5 | 106.0 | 91.9 | 100.8 |
| 24 | ABL1 | 9.3 | 77.6 | 68.0 | 97.6 | 104.5 | 106.7 | 107.1 | 109.3 | 84.9 | 92.5 |
| 25 | GSG2 | 9.0 | 69.9 | 69.9 | 88.0 | 89.5 | 101.8 | 98.6 | 109.6 | 87.8 | 89.8 |
| 26 | MAP2K1 | 11.5 | 79.8 | 74.1 | 100.7 | 103.1 | 110.4 | 106.6 | 104.7 | 66.1 | 72.0 |
| 27 | OXSR1 | 15.8 | 106.2 | 100.3 | 111.2 | 109.4 | 110.1 | 110.7 | 115.9 | 94.7 | 101.6 |
| 28 | MAP3K7 | 9.5 | 37.5 | 27.8 | 84.2 | 70.7 | 98.6 | 93.3 | 103.4 | 69.4 | 63.5 |
| 29 | AXL | 8.8 | 35.4 | 26.8 | 60.9 | 60.3 | 77.2 | 85.1 | 100.0 | 37.6 | 46.3 |
| 30 | PRKACA | 10.4 | 13.9 | 18.6 | 40.8 | 32.6 | 38.3 | 65.9 | 81.1 | 24.6 | 26.4 |
| 31 | INSR | 16.2 | 23.1 | 32.8 | 72.3 | 69.1 | 84.8 | 93.6 | 97.9 | 79.1 | 83.1 |
| 32 | SRPK1 | 17.7 | 24.4 | 38.9 | 65.3 | 61.1 | 85.0 | 80.8 | 95.7 | 78.5 | 78.3 |
| 33 | EGFR | 23.5 | 30.5 | 82.2 | 107.6 | 93.1 | 108.4 | 95.4 | 109.5 | 96.2 | 102.2 |
| 34 | MAPKAPK2 | 27.6 | 73.3 | 91.8 | 105.4 | 95.3 | 108.4 | 104.1 | 106.1 | 92.5 | 94.6 |
| 35 | PLK1 | 26.5 | 93.8 | 80.9 | 103.5 | 99.2 | 104.1 | 99.7 | 97.9 | 95.9 | 97.7 |
| 36 | STK16 | 52.5 | 59.0 | 51.6 | 94.0 | 86.7 | 99.8 | 101.3 | 104.6 | 103.2 | 94.0 |
| 37 | RPS6KB1 | 7.8 | 7.9 | 9.2 | 15.0 | 11.8 | 15.2 | 25.2 | 72.4 | 11.1 | 11.8 |
| 38 | STK4 | 5.5 | 1.8 | 1.9 | 6.0 | 5.5 | 12.0 | 10.9 | 72.8 | 1.5 | 2.7 |
| 39 | FGFR2 | 6.5 | 9.8 | 9.2 | 26.5 | 21.7 | 43.2 | 45.8 | 88.4 | 26.5 | 31.4 |
| 40 | RPS6KA5 | 1.1 | 1.7 | 1.8 | 3.3 | 2.4 | 1.6 | 8.6 | 61.4 | 5.2 | 7.4 |

Example 3 Type-S Protein Kinase Inhibitors can Reduce Survival Rates of Gastric Cancer Cells Previous studies discovered that protein kinase FGFR2 (hereinafter abbreviated as FGFR2) over-expressed in gastric cancer cells, whereas compound 4 of the present invention had an inhibitory effect on FGFR2. Hence, compound 4 of the present invention in the test had an inhibitory effect on gastric cancer cells. Gastric cancer cell line MKN-45 was incubated on a 96-well plate (about $1 \times 10^4$ cells/well). After the cells adhered, the 96-well plate was replaced with serum-free culture media, and different concentrations (from 40 to 0.039 µM) of drugs were added. After incubating at 37° C. for 24 hours, PBS was used for washing three times, and MTT culture media was added to react with cells. Violet crystals appeared after two hours. Then, DMSO (50 µl) was added to terminate the reaction. A light-absorbing microvolume spectrophotometer (ELISA reader) was used, and an absorption value of 570 nm was obtained. A blank value was deducted from each of the obtained absorbance values, and then the difference was divided by the value of the control group to calculate a percentage, i.e., a cell survival rate. The experiment was repeated three times to obtain an average value and a standard deviation. As shown by the results in Table 2, compound 4 of the present invention showed an $IC_{50}$ value of 1.6 µM for inhibiting gastric cancer cell line MKN-45 (which over-expressed FGFR2).

The foregoing examples are provided only to illustrate the principle and effect of the present invention, and they do not limit the scope of the present invention. It should be understood to one skilled in the art that, modifications and alterations can be made to the examples, without departing from the spirit and principle of the present invention. Therefore, the equivalent modifications or alterations achieved by a one skilled in the art, without departing from the spirit and technical principle of the present invention, should still be encompassed by the following appended claims.

The invention claimed is:

1. A compound of formula (I) or the salt thereof:

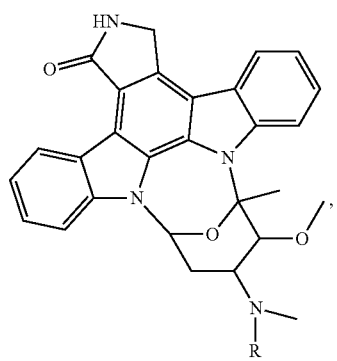

(I)

wherein R is one selected from the group consisting of

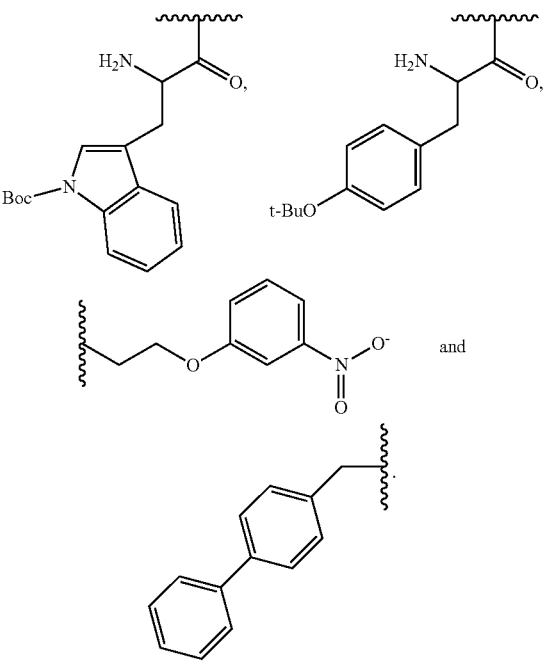

and

2. A pharmaceutical composition, comprising a compound of formula (I) or a salt and a pharmaceutically acceptable carrier thereof.

3. A method for treating gastric cancer by inhibiting a protein kinase comprising administrating the compound of claim 1 to a subject in need thereof, wherein the protein kinase is a type-S protein kinase inhibiting growth of gastric cancer cells, and the compound is a type-S protein kinase inhibitor which binds to an ATP-binding site and a substrate-recognition site of the protein kinase simultaneously to inhibit the protein kinase.

4. The method of claim 3, wherein the type-S protein kinase is at least one selected from the group consisting of LIMK1, ALK, PDPK1, AURKA, LCK, RET, PIM1, DYRK1A, MERTK, DAPK1, CHEK2, IRAK4, JAK2, GSK3B, CAMK2D, AKT1, PAK4, CLK1, BTK, KDR, FGFR1, CDK2, MAP3K7, AXL, PRKACA, INSR, SRPK1, EGFR, RPS6KB1, STK4, FGFR2 and RPS6KA5.

5. The method of claim 3, wherein the compound has an $IC_{50}$ value of from 1.0 µM to 2.0 µM for the inhibition of the gastric cancer cells.

* * * * *

UNITED STATES PATENT AND TRADEMARK OFFICE
CERTIFICATE OF CORRECTION

PATENT NO. : 9,738,660 B2
APPLICATION NO. : 14/599349
DATED : August 22, 2017
INVENTOR(S) : Jinn-Moon Yang et al.

Page 1 of 1

It is certified that error appears in the above-identified patent and that said Letters Patent is hereby corrected as shown below:

On the Title Page

Item (73), "(CN)" should be deleted from the Assignee country

Signed and Sealed this
Fifth Day of December, 2017

Joseph Matal
*Performing the Functions and Duties of the
Under Secretary of Commerce for Intellectual Property and
Director of the United States Patent and Trademark Office*